US 9,572,637 B2

(12) United States Patent
Jinkyun (10) Patent No.: US 9,572,637 B2
(45) Date of Patent: Feb. 21, 2017

(54) APPARATUS FOR GENERATING DENTAL DATA FOR MANUFACTURING AN ALIGNER AND METHOD OF MANUFACTURING CLEAR ALIGNER USING THE APPARATUS

(71) Applicant: Lee Jinkyun, Dongjak-gu (KR)

(72) Inventor: Lee Jinkyun, Dongjak-gu (KR)

(*) Notice: Subject to any disclaimer, the term of this patent is extended or adjusted under 35 U.S.C. 154(b) by 0 days.

(21) Appl. No.: 14/706,848

(22) Filed: May 7, 2015

(65) Prior Publication Data
US 2016/0120617 A1 May 5, 2016

(30) Foreign Application Priority Data

Nov. 3, 2014 (KR) .................. 10-2014-0151329

(51) Int. Cl.
| A61C 7/00 | (2006.01) |
| A61C 7/08 | (2006.01) |
| A61B 6/03 | (2006.01) |
| A61B 6/14 | (2006.01) |
| A61B 6/00 | (2006.01) |

(Continued)

(52) U.S. Cl.
CPC .............. *A61C 7/002* (2013.01); *A61B 6/032* (2013.01); *A61B 6/14* (2013.01); *A61B 6/4078* (2013.01); *A61C 7/08* (2013.01); *A61C 9/0046* (2013.01); *A61C 2007/004* (2013.01); *B33Y 10/00* (2014.12); *B33Y 30/00* (2014.12); *B33Y 50/00* (2014.12); *B33Y 80/00* (2014.12)

(58) Field of Classification Search
CPC combination set(s) only.
See application file for complete search history.

(56) References Cited

U.S. PATENT DOCUMENTS 6,227,850 B1* 5/2001 Chishti .................... A61C 7/00
433/213
7,077,646 B2* 7/2006 Hilliard .................... A61C 7/00
433/18

(Continued)

FOREIGN PATENT DOCUMENTS

| EP | 1 474 062 | 4/2011 |
| JP | 2014-91047 | 5/2014 |

(Continued)

OTHER PUBLICATIONS

European Search Report for EP 15167210.2, mailed Nov. 16, 2015, 8 pages.

(Continued)

*Primary Examiner* — Anand Bhatnagar
(74) *Attorney, Agent, or Firm* — Morrison & Foerster LLP (57) ABSTRACT

Provided is an apparatus for generating dental data for manufacturing an aligner, the apparatus including: a dental-data generation unit, in which the dental-data generation unit includes a preprocessing module includes a first module that receives data on a current state of the teeth of the patient from a scanner that scans the current state of the teeth of the patient, a second module that generates a state of the teeth of the patient and the vicinity of the teeth as 3D data, based on the data received from the scanner, a third module that sets a central point for dental movement in the 3D data, a fourth module that sets each central reference for a crown, a buccal surface, and a lingual surface of the tooth in the 3D data, and a fifth module that sets a reference for a dental root point in the 3D data.

16 Claims, 7 Drawing Sheets

(51) Int. Cl.
*A61C 9/00* (2006.01)
*B33Y 10/00* (2015.01)
*B33Y 30/00* (2015.01)
*B33Y 50/00* (2015.01)
*B33Y 80/00* (2015.01)

(56) References Cited

U.S. PATENT DOCUMENTS

| | | | | |
|---|---|---|---|---|
| 7,746,339 | B2* | 6/2010 | Matov | A61C 19/04 345/419 |
| 7,880,751 | B2* | 2/2011 | Kuo | A61C 7/00 345/629 |
| 8,021,147 | B2* | 9/2011 | Sporbert | A61C 7/00 433/24 |
| 8,296,952 | B2* | 10/2012 | Greenberg | A61C 7/08 29/896.11 |
| 2005/0048433 | A1* | 3/2005 | Hilliard | A61C 7/00 433/24 |
| 2008/0248443 | A1* | 10/2008 | Chishti | A61C 7/00 433/24 |
| 2009/0113714 | A1* | 5/2009 | Greenberg | A61C 7/08 29/896.11 |
| 2009/0191503 | A1 | 7/2009 | Matov et al. | |
| 2013/0230818 | A1* | 9/2013 | Matov | A61C 7/00 433/3 |

FOREIGN PATENT DOCUMENTS

| | | |
|---|---|---|
| KR | 10-0583183 | 8/2005 |
| KR | 10-1218390 | 1/2013 |
| KR | 10-2013-0048202 | 5/2013 |
| KR | 10-1295610 | 8/2013 |

OTHER PUBLICATIONS

Allowance of Patent (translation) for KR 10-2014-0151329, mailed Mar. 12, 2015, 2 pages.

\* cited by examiner

APPARATUS FOR GENERATING DENTAL DATA FOR MANUFACTURING AN ALIGNER AND METHOD OF MANUFACTURING CLEAR ALIGNER USING THE APPARATUS

CROSS-REFERENCE TO RELATED APPLICATIONS

Pursuant to 35 U.S.C. §119(a), this application claims the benefit of earlier filing date and right of priority to Korean Application No. 10-2014-0151329, filed on Nov. 3, 2014, the contents of which are incorporated by reference herein in its entirety.

BACKGROUND OF THE INVENTION

1. Field of the Disclosure

The present disclose relates to an apparatus for generating dental data for manufacturing an aligner using data using a CT apparatus, and a method of manufacturing a clear aligner using the apparatus.

2. Background of the Disclosure

Generally, a dental alignment method is categorized into a dental alignment method that uses a metal alignment device, a lingual-side alignment method in which an aligner is placed in an oral cavity, and a transparency alignment method in which a clear aligner made of transparent material is attached to teeth for dental alignment.

Particularly, the transparency alignment method is one in which the clear aligner made of transparent material covers teeth. In this method, the aligner is not seen from the outside and is detachably attached to the teeth. Thus, the method is gaining popularity due to its comfortability when compared to other alignment methods.

However, in the clear alignment method in the related art, in a case where there is a dentist's request to manufacture a clear aligner, using an apparatus for generating data on an alignment target tooth, data on multiple alignment target teeth that have to be arranged according to dental movement is generated from dental data on a patient that results from scanning by an 3D scanner. Then, a cast of the teeth is formed by 3D-printing the generated data on the alignment target tooth, and the clear aligner that is capable of performing dental alignment in multiple stages is manufactured by pressing transparent films against the cast of the teeth using a laminator.

At this point, the apparatus for generating data on an alignment target tooth has to separate the teeth from each other at a real-world separation distance between the teeth in a real-world shape, but fails to do so. Thus, an error occurs when the data on the alignment target tooth is generated.

In addition, in a case where the teeth are moved, in most cases, after the dental alignment is performed, one portion of the teeth is moved up out of a gum or moved down into the gum. Therefore, when a method of predicting and setting the dental movement is employed, in a case where only a portion of the tooth that is above the gum is a target for the dental movement, there is a problem in that the tooth is not moved sufficiently far in an intended direction due to a gum or a gum bone or the tooth is difficult to align with precision due to the interference of other teeth.

To solve this problem, an apparatus for generating dental data for manufacturing a clear aligner, which employs a mechanism by which to move the tooth, and a method of manufacturing the clear aligner using the apparatus are considered.

SUMMARY OF THE INVENTION

Therefore, an aspect of the detailed description is to provide an apparatus for generating dental data for manufacturing an aligner, which is capable of performing dental movement with precision, and a method of manufacturing a clear aligner using the apparatus.

Another aspect of the detailed description is to provide an apparatus for generating dental data for manufacturing an aligner, which is capable of manufacturing the aligner using a 3D printer, and a method of manufacturing a clear aligner using the apparatus.

To achieve these and other advantages and in accordance with the purpose of this specification, as embodied and broadly described herein, there is provided an apparatus for generating dental data for manufacturing an aligner, the apparatus including: a dental-data generation unit that generates data on an alignment target tooth in multiple stages based on a current arrangement of teeth of a patient, in which the dental-data generation unit includes a preprocessing module that includes a first module that receives data on a current state of the teeth of the patient from a scanner that scans the current state of the teeth of the patient, a second module that generates a state of the teeth of the patient and the vicinity of the teeth as 3D data, based on the data received from the scanner, a third module that sets a central point for dental movement in the 3D data, a fourth module that sets each central reference for a crown, a buccal surface, and a lingual surface of the tooth in the 3D data, and a fifth module that sets a reference for a dental root point in the 3D data.

In the apparatus, the scanner may be a fan beam computed tomography (fan beam CT) apparatus.

In the apparatus, data that is received from the fan beam apparatus may include first data for expressing a state where the teeth are engaged with each other in order to check shapes of the teeth that are engaged with each other, and second data for expressing a state where a wax is attached to a gingiva or a mouthpiece is inserted into an oral cavity of the patient in such a manner that a space is secured between the gingiva and adjacent lips, in order to check a thickness of the gingiva.

In the apparatus, the second module may recognize the thickness of the gingiva based on the first data and the second data, and thus may generate the 3D data for expressing the teeth and an alveolar bone that encloses the teeth, along with the gingiva that encloses the alveolar bone.

In the apparatus, the teeth, the alveolar bone, and the gingiva may be expressed in different colors.

In the apparatus, the second module may be configured in such a manner that an upper jaw and a lower jaw are separated from each other in the 3D data.

In the apparatus, in the 3D data, the second module may separate the teeth of the patient from each other as units of dental movement, and then recognizes the teeth individually in such a manner that each of the teeth is able to be moved.

In the apparatus, when setting the central point for dental movement, the third module may recognize the tooth, the alveolar bone that encloses the tooth, and the gingiva that encloses the alveolar bone, and may set the central point for dental movement.

The apparatus may further include a sixth module that moves the tooth by a predetermined distance from the central point for dental movement.

In the apparatus, the third module may move the tooth by the predetermined distance, and then may newly set the central point for dental movement based on data on the moved tooth.

In the apparatus, the sixth module may move a dental periodontal complex that includes the tooth, the alveolar bone that encloses the tooth, and the gingiva that encloses the alveolar bone.

In the apparatus, a contour of the face of the patient that will result after dental alignment is performed may be predicted based on a state of the teeth that results after the dental alignment is performed, using data that is obtained by a fan beam CT apparatus, and the patient may view changes over time in a state of the vicinity of the lip or the mouse in order to determine the extent of the change.

In the apparatus, data on a photograph of the patient may be combined with the current state of the teeth of the patient to express in detail a state of the teeth that will result after dental alignment is performed.

In the apparatus, the scanner may be a cone beam computed tomography apparatus. In the apparatus, the scanner may be a panoramic X-ray (panoramic radiograph) apparatus. In the apparatus, the scanner may be a 3D scanner for scanning an oral cavity.

In the apparatus, the data that is used, as basic data, by the second module may include the data that is received from the scanner, and data that is obtained, as a supplement to the data that is received from the scanner, by modelling a plaster cast of an oral cavity of the patent.

In the apparatus, when setting the root of the tooth and the central point for movement of the tooth, the central point for movement may be set to be positioned on a lower portion of the alveolar bone of the patient.

In the apparatus, in a case where the tooth, the central point for dental movement of which is set, is a single-rooted tooth, the central point for dental movement may be positioned a distance of 40% to 42% of the root of the tooth enclosed by the alveolar bone downward from the top of the alveolar bone.

In the apparatus, in a case where the tooth, the central point for dental movement of which is set, is a multi-rooted tooth, the central point for dental movement may be positioned a distance of between 1 and 2 mm downward from a furcation from which the root of the tooth bifurcates.

According to another aspect of the present invention, there is provided a method of manufacturing a clear aligner using an apparatus for generating dental data for manufacturing an aligner, the method including: receiving data on a current state of teeth of a patient from a scanner that scans the current state of teeth of the patient; generating 3D data on a state of an oral cavity, based on the data; separating an upper jaw and a lower jaw from each other in the 3D data; setting a central point for dental movement to be on a root of a tooth in a state where the upper jaw and the lower jaw is separated from each other; generating 3D data on the tooth that is moved a predetermined distance from the central point for dental movement; and manufacturing the clear aligner based on the 3D data on the moved tooth.

In the method, the 3D data on the tooth may be data on a dental periodontal complex that includes the tooth, an alveolar bone, and a gingiva.

The method may further include separating teeth from each other and individually recognizing the teeth as units of dental movement after separating the upper jaw and the lower jaw.

In the method, in the generating of the 3D data on the tooth, the dental periodontal complex may be moved in such a manner that dental alignment is performed with high precision.

In the method, in the generating of the 3D data on the tooth, a distance that an alignment target tooth is moved for one month may be set to 1.0 to 1.5 mm, multiple pieces of 3D data on the alignment target tooth may be generated every predetermined period of time, and a moved state of the alignment target tooth and the contour of the face of the patient may be generated.

In the method, in the generating of the 3D data on the tooth, after each dental periodontal complex is moved for a predetermined period of time, the central point for dental movement may be newly set based on the moved dental periodontal complex.

In the method, in the dental periodontal complex, the teeth, the alveolar bone, and the gingiva of the patient may be expressed in different colors.

The method may further include setting a central reference point to be on a crown, a buccal surface, and a lingual surface of each tooth after the setting of the central point for dental movement In the method, the clear aligner may be manufactured using any one of a method of sintering PET powder using a laser, a method of layering PET filaments using heat or adhesive, or a method of forming the PET filaments into a shape of the clear aligner above a melting point using a 3D printer and then solidifying the clear aligner.

In the method, the clear aligner may be manufactured by forming liquid-state PET into a specific shape based on the data, using a laser.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE INVENTION

Description will now be given in detail of the exemplary embodiments, with reference to the accompanying drawings. For the sake of brief description with reference to the drawings, the same or equivalent components will be provided with the same reference numbers, and description thereof will not be repeated.

An apparatus for generating dental data for manufacturing an aligner and a method of manufacturing a clear aligner using the apparatus for generating dental data for manufacturing an aligner according to embodiments of the present invention will be described below referring to the accompanying drawings. It is apparent to a person of ordinary skill in the art that other specific embodiments of the present invention may be constructed within a range that does not depart from the nature and gist of the present invention.

Figure 1:
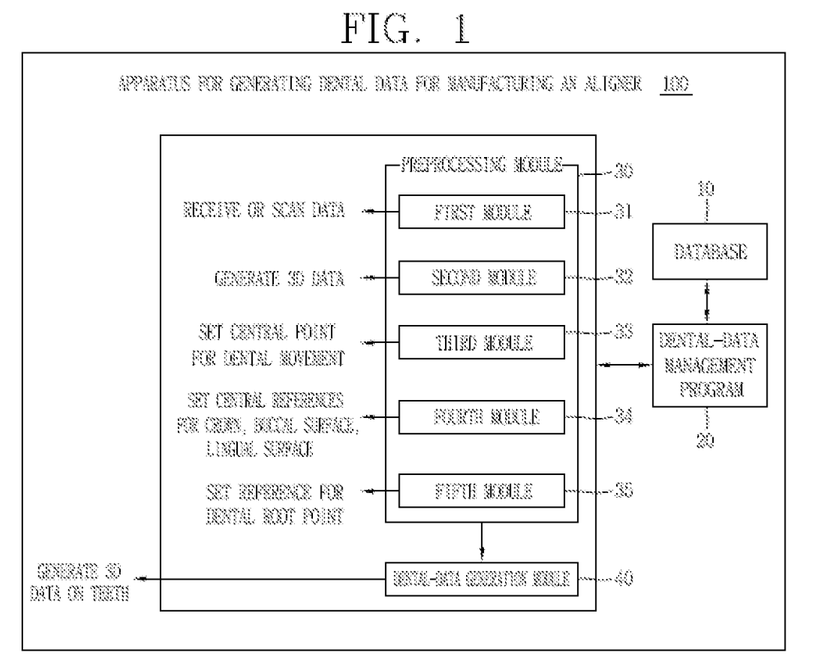
FIG. 1 is a systematic configuration diagram that schematically illustrates an apparatus for generating dental data for manufacturing an aligner according to an embodiment of the present invention.

FIG. 1 is a systematic configuration diagram that schematically illustrates an apparatus 100 for generating dental data for manufacturing an aligner according to an embodiment of the present invention.

The apparatus 100 for generating dental data for manufacturing an aligner is an apparatus that generates data relating to alignment target teeth in multiple steps based on a current arrangement of teeth of a patient.

The apparatus 100 for generating dental data for manufacturing an aligner includes a database 10, a dental-data management program 20, a preprocessing module dental-data generation unit 30, and a dental data generation module 40.

The database 10 stores and manages pieces of alignment data that are generated, such as pieces of pre-alignment and post-alignment contour data, guide information, and the like.

The dental alignment data management program 20 provides interfaces for functions of units and modules of the apparatus 100 for generating dental data for manufacturing an aligner.

The preprocessing module dental-data generation unit 30 includes a preprocessing module that generates the dental data for manufacturing the aligner Preprocessing of the current dental data on the patient that is performed by the preprocessing module in order to generate the dental data for manufacturing the aligner will be described below.

A first module 31 receives data on a current dental state of the patient from a scanner that scans the current dental state of the patient. At this time, it is desirable that the scanner use a fan beam computed tomography (fan beam CT) apparatus. The fan beam CT obtains information suitable for generating 3D data by making an X-ray of selected planes of an oral cavity of the patient in multiple directions.

On the other hand, the scanners is a cone beam computed tomography (cone beam CT) apparatus, a panoramic X-ray (panoramic radiography) apparatus, or a 3D scanner. In the case of the cone beam CT apparatus, there is a likelihood that information relating to teeth of the patent will not be obtained. Thus, as a supplement to data that is received from the cone beam CT apparatus, data that is obtained by modelling a plaster cast of the oral cavity of the patent is included.

A second module 32 generates 3D data on a state of the teeth of the patient and the vicinity of the teeth, based on the data that is received from the scanner.

That is, the 3D data on the state of the teeth of the patient and the vicinity of the teeth is generated based on the data that is obtained by the fan beam CT apparatus, the cone beam CT apparatus, the panoramic X-ray apparatus, or the 3D scanner, and the data that is obtained by scanning the plaster cast of the oral cavity. It is desirable that the teeth and the vicinity of the teeth include a crown, a dental root, a gingiva, and an alveolar bone.

In addition, prediction of a shape of the dental root of the patient in a case of using the data obtained by the panoramic X-ray apparatus and the data that is obtained by scanning the plaster cast of the oral cavity is described below.

When the data that is obtained by scanning the plaster cast of the oral cavity of the patient is cut along a border between the crown and the dental root, data on a cross section of the dental root is obtained. A cross-section of the dental root is predicted in this manner. This is done because a cross section of the dental root is not available from the data obtained by the panoramic X-ray apparatus.

A third module 33 sets a central point for dental movement in the 3D data.

The dental alignment according to the present invention is performed by using a method of rotating the tooth about the central point for dental movement. In this respect, it is important to set the central point for dental movement.

The central point for movement of a single-rooted tooth with one root is set to approximately a point that is positioned a distance of 40 to 42% of the length of the dental root downward from the top of the dental root that is supported by the alveolar bone. That is, a point that is positioned a distance of approximately 40 to 42% of the entire length of the buried dental root downward from the top of the alveolar bone that encloses the teeth is the central point for dental movement.

The central point for movement of a multi-rooted tooth with two roots is positioned a distance of approximately 1 to 2 mm downward from a furcation from which the root of the tooth bifurcates.

A fourth module 34 sets each central reference for a crown, a buccal surface, and a lingual surface of a tooth in the 3D data. The central references are used as data for setting an entire size of each tooth and for setting positional information on each tooth.

A fifth module 35 sets a reference for a dental root point in the 3D data. A reference for the central point for movement of each dental root is set based on each central reference for the crown, the buccal surface, and the lingual surface of the tooth.

Figure 2:
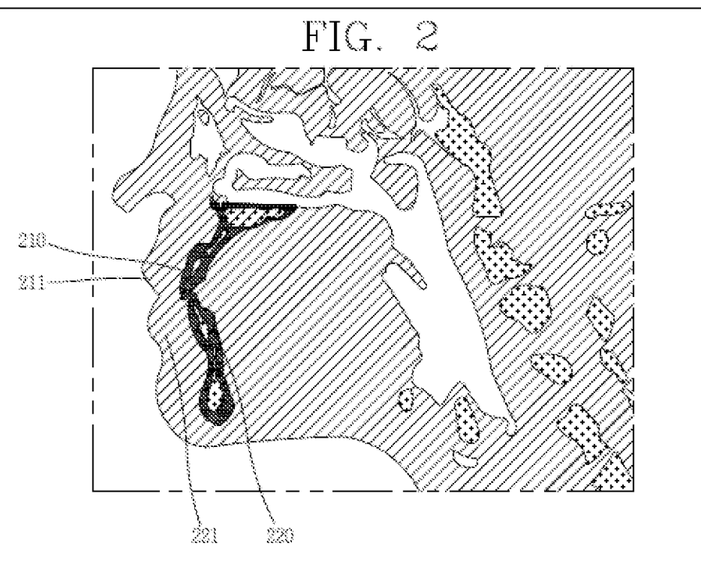
FIGS. 2 and 3 are diagrams illustrating, each some of the pieces of data that are obtained by scanning a head of a patient using a fan beam computed tomography (fan beam CT) apparatus, according to the embodiment of the present invention.
Figure 3:
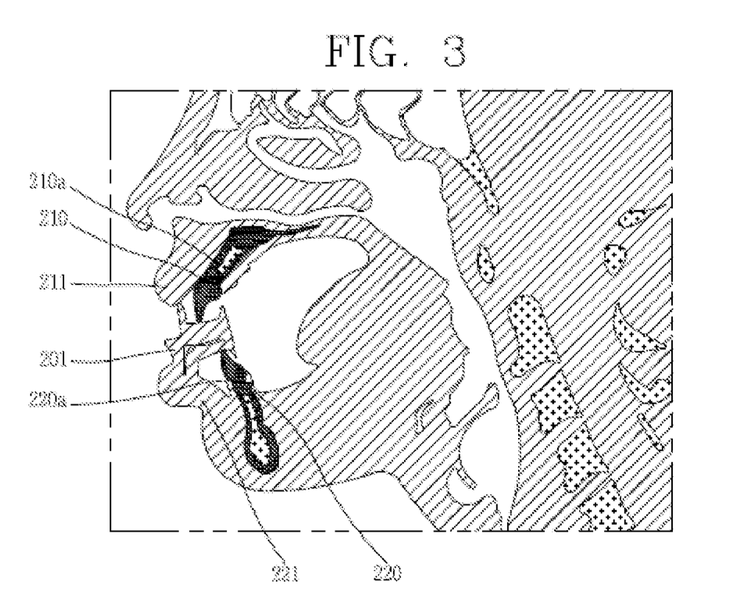

FIGS. 2 and 3 are diagrams, each illustrating some of the pieces of data obtained by the fan beam computed tomography (fan beam CT) apparatus according to the embodiment of the present invention.

FIG. 2 is an image captured using the fan beam CT in a state where an upper tooth 210 and a lower tooth 220 of the patient are brought into contact with each other. FIG. 3 is an image captured using the fan beam CT with a mouthpiece being inserted into the oral cavity of the patient.

3D data is generated based on two pieces of data. One piece is FIG. 2 serving as first data, and the other is FIG. 3 serving as second data.

The first data is for expressing a state where the teeth 210 and 220 are engaged with each other in order to check shapes of the teeth 210 and 220 that are engaged with each other. The second data is for expressing a state where a wax is attached to a gingiva 210a or a mouthpiece is inserted into the oral cavity of the patient in such a manner that a space is secured between the gingiva 210a and adjacent lips 211 and 221, in order to check a thickness of the gingiva 210a.

At this point, the second module recognizes the thickness of the gingiva 210a based on the first data and the second data, and thus generates the 3D data for expressing the teeth 210 and 220 and the alveolar bone that encloses the teeth 210 and 220, along with the gingiva 210a that encloses the alveolar bone. This is because the expressing of the alveolar bone and the gingiva 210a as well as the teeth 210 and 220 plays an important role in setting the central point for movement of each of the teeth 210 and 220 or for movement of the dental root.

In addition, the teeth 210 and 220, the alveolar bone, and the gingiva 210a are distinguishably expressed in different colors.

The second module is configured such that, in the 3D data, an upper jaw (a portion including the upper tooth 210) and a lower jaw (a portion including the lower tooth 220) are separable.

Figure 4:
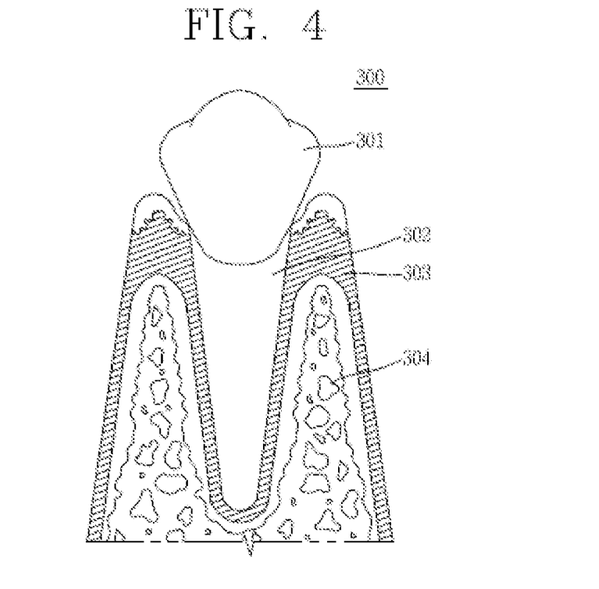
FIG. 4 is a cross-sectional diagram of a dental periodontal complex.

FIG. 4 is a cross-sectional diagram of a dental periodontal complex 300.

The dental periodontal complex 300 includes teeth, an alveolar bone 304, and a gingiva 303. The tooth includes a crown 301 and a dental root 302. The alveolar bone 304 refers to a gum bone that encloses the dental root 302. The gingiva 303 refers to a gum between the teeth and the alveolar bone 304.

The alveolar bone 304 and the gingiva 303 are moved together while the alignment is in progress. Therefore, the recognition of the dental movement as movement of the dental periodontal complex is an important factor in recognizing the dental alignment as a whole.

Figure 5:
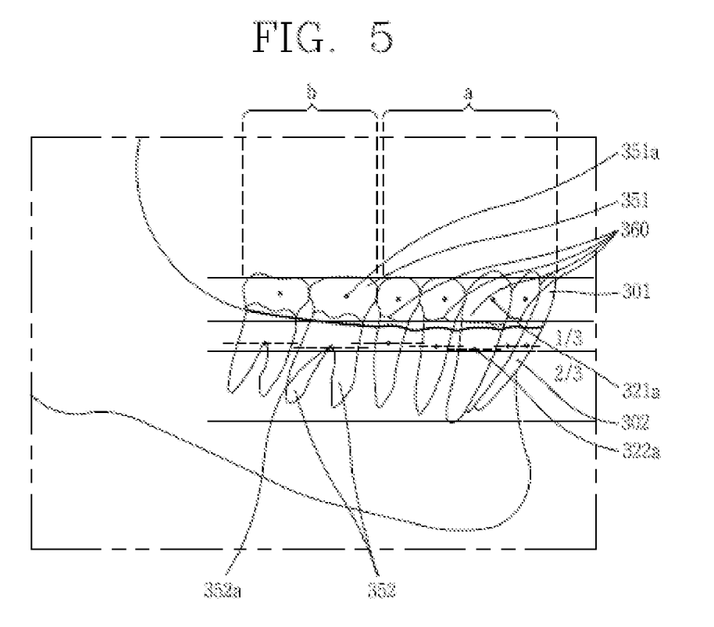
FIG. 5 is a diagram illustrating teeth and a periodontal membrane(complex) in a lower jaw, and each central point for dental movement.

FIG. 5 is a diagram illustrating teeth and a periodontal membrane(complex) in the lower jaw, and each central point 322a for dental movement.

As one example, a single-rooted tooth 301 with one root is described. The third module of the apparatus for generating dental data for manufacturing an aligner according to the present invention recognizes a tooth, an alveolar bone that encloses the tooth, and a gingiva (not illustrated) that encloses the alveolar bone in order to set a central point 322a for dental movement, and then sets the central point 322a for dental movement. When only a tooth that is above a gum line 360 is aligned, the alveolar bone 304 and the gingiva are moved together, and thus an error in alignment occurs.

Therefore, when setting the central point 322a for dental movement, the third module recognizes the tooth, the alveolar bone that encloses the tooth, and the gingiva 210a that encloses the alveolar bone, and sets the central point 322a for dental movement. It is necessary to set the central point 322a for dental movement in a unit of the dental periodontal complex 300 (refer to FIG. 4) for reduction in error and more precise alignment.

In addition, the apparatus for generating dental data for manufacturing an aligner may further include a sixth module that moves the tooth by a predetermined distance from the central point 322a for dental movement.

When setting the dental root 302 and the central point 322a for dental movement, the central point 322a for dental movement is set to be positioned below the alveolar bone 304. It is desirable that the central point 322a for dental movement be positioned at a point that is positioned a distance of 40 to 42% of the entire length of the dental root downward from the gum line 360. Otherwise, the central point 322a for dental movement may be set to a point that is positioned a distance of approximately one third of the entire length of the dental root downward from the gum (gingival) line 360.

At this time, in a case where a tooth, the central point 322a for dental movement of which is set, is a single-rooted tooth with one root, the central point 322a for dental movement is positioned a distance of 40% to 42% of the root of the tooth enclosed by the alveolar bone downward from the top of the alveolar bone.

Otherwise, in a case where a tooth, the central point 352a for dental movement of which is set, is a multi-rooted tooth, the central point 352a for dental movement is positioned a distance of between 1 and 2 mm downward from the furcation from which the root of the tooth bifurcates.

Figure 6A:
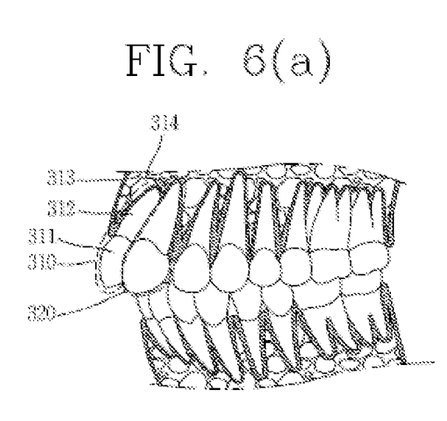
FIGS. 6(a) and 6(b) are diagrams of a pre-movement dental periodontal complex when viewed from the side and when viewed from the front, respectively.
Figure 6B:
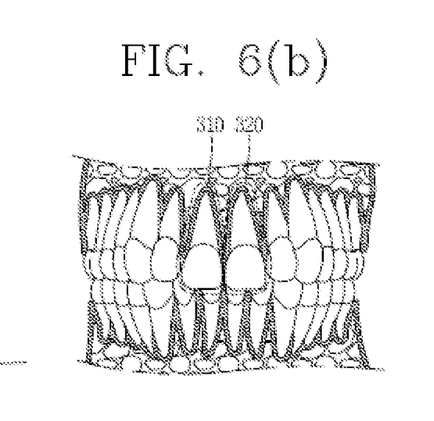
Figure 7A:
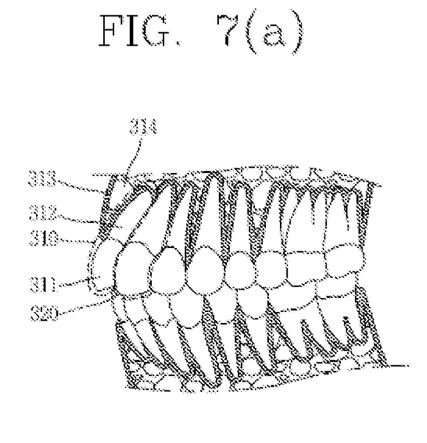
FIGS. 7(a) and 7(b) are diagrams of a post-movement dental periodontal complex when viewed from the side and when viewed from the front, respectively.
Figure 7B:
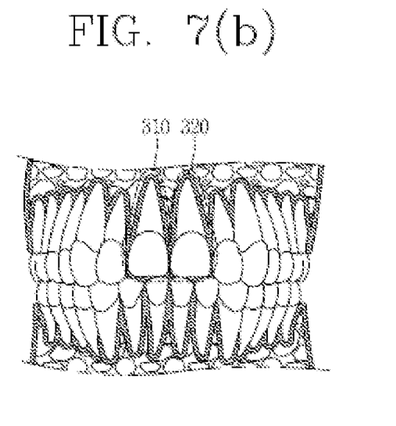

FIGS. 6(a) and 6(b) are diagrams of the pre-movement dental periodontal complex when viewed from the side and when viewed from the front, respectively. FIGS. 7(a) and 7(b) are diagrams of the post-movement dental periodontal complex when viewed from the side and when viewed from the front, respectively.

In the 3D data, the second module of the apparatus for generating dental data for manufacturing an aligner according to the present invention separates teeth of the patient from each other as units of dental movement, and then recognizes the teeth individually in such a manner that each of the teeth can be moved.

In addition, the third module moves the tooth by a predetermined distance, and then newly sets the central point for dental movement based on data on the moved tooth.

Then, the sixth module moves the dental periodontal complex that includes the tooth, the alveolar bone that encloses the tooth, and the gingiva that encloses the alveolar bone.

Specifically, referring to FIG. 6(a), a first dental periodontal complex 310 and a second dental periodontal complex 320 are individually set to be units of dental movement. Then, the two dental periodontal complexes 310 and 320 are set in such a manner that the two dental periodontal complexes 310 and 320 are moved. When the two dental periodontal complexes are moved, adjacent dental periodontal complexes are organically moved in conjunction with the two dental periodontal complexes 310 and 320. Therefore, more precise dental alignment data is generated.

Figure 8:
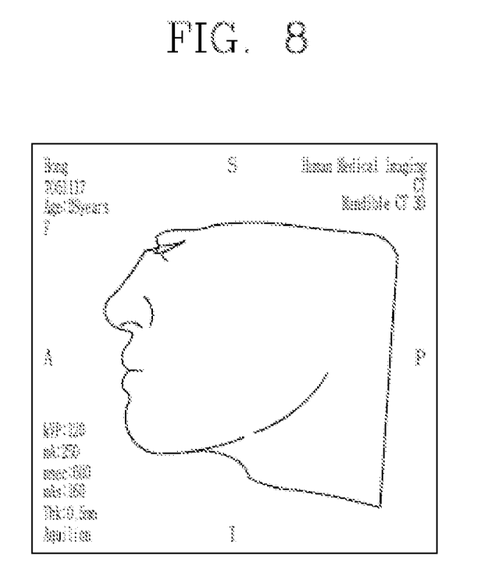
FIG. 8 is a diagram illustrating an image of the patient's face, which is captured using the fan beam CT apparatus.

FIG. 8 is a diagram illustrating an image of the patient's face, which is captured using the fan beam CT apparatus.

Material that is obtained using the fan beam CT apparatus includes data on a photograph of the patient. In addition, the data on the photograph of the patient may be combined with the material obtained using the fan beam CT apparatus to express in detail a state of teeth that will result after the dental alignment is performed.

Figure 9:
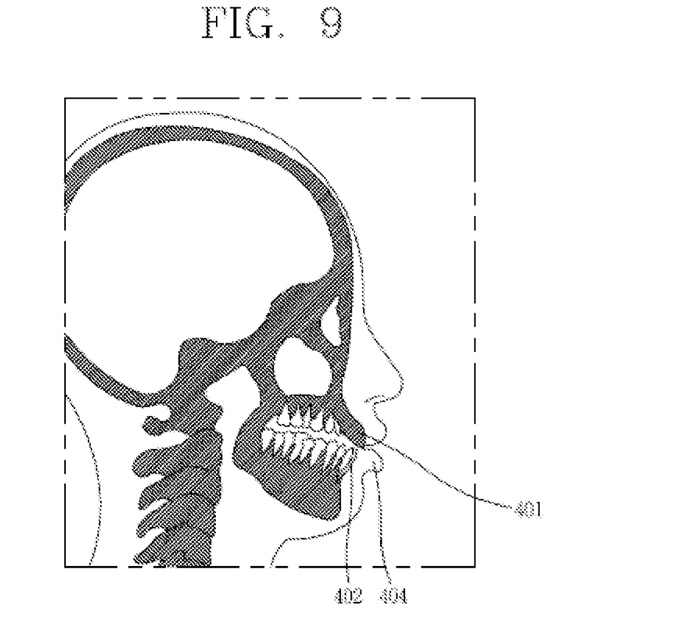
FIG. 9 is a diagram illustrating a state of teeth of the patient that is given before dental alignment is performed, which is obtained using an X-ray apparatus.
Figure 10:
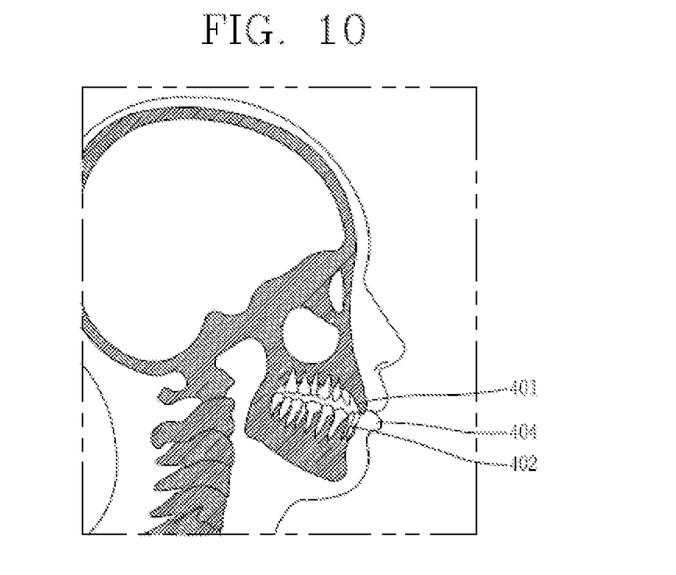
FIG. 10 is a diagram illustrating a state of teeth of the patient that will result after the dental alignment is performed, which is obtained using the X-ray apparatus.

FIG. 9 is a diagram illustrating a state of teeth of the patient that is given before the dental alignment is performed, which is obtained using the X-ray apparatus. FIG. 10 is a diagram illustrating a state of teeth of the patient that will result after the dental alignment is performed, which is obtained using the X-ray apparatus.

The scanners include the X-ray apparatus that scans a current state of teeth of a patient. Then, in a case where the sixth module moves the dental periodontal complex, CT apparatus-generated data on the state of teeth that will result after the dental movement or data on the state of teeth that will result after the dental movement is generated. The state of teeth that will result after the dental alignment is performed can be predicted based on the generated data.

In addition, for the prediction of the state of teeth of the patient that results after the dental alignment is performed, in addition to X-ray apparatus-generated data, data on the state of teeth that will result after the dental alignment is performed may be generated using the CT apparatus-generated data.

Specifically, FIG. 9 illustrates a state of an upper tooth 401, a lower tooth 402, and a lip 404 of the patient. FIG. 10 illustrates a state of teeth of the patient that will result after the dental alignment is performed. FIG. 10 illustrates that the upper tooth 401, the lower tooth 402, and the lip 404 are moved inward toward the face of the patient, compared with those in FIG. 9.

Figure 11:
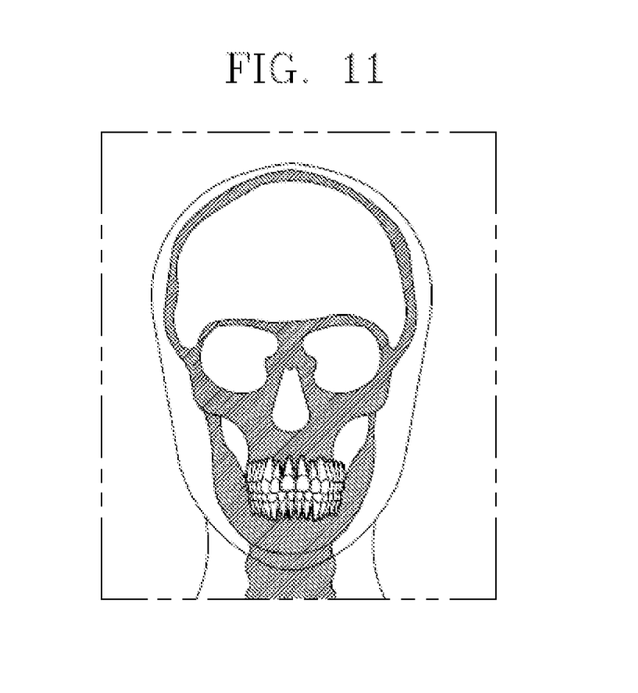
FIG. 11 is a diagram illustrating an image that is captured using the X-ray apparatus.
Figure 12:
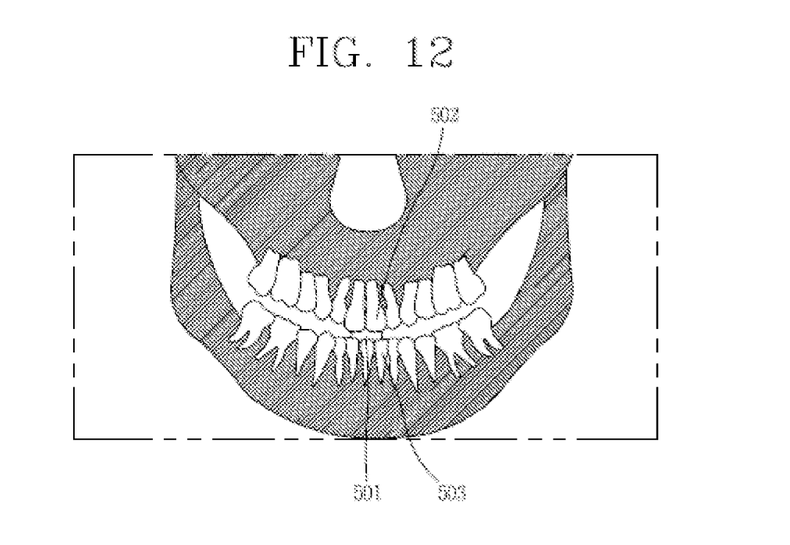
FIG. 12 is a diagram illustrating an image of an oral cavity of the patient, which is obtained using a panoramic X-ray apparatus.

FIG. 11 is a diagram illustrating an image that is captured using X-ray. FIG. 12 is a diagram illustrating an image of an oral(oral) cavity of the patient, which is obtained using the panoramic X-ray apparatus.

As described above, the scanners that scan the current state of teeth of the patient include an X-ray apparatus and the panoramic X-ray apparatus. However, in a case where the X-ray apparatus or the panoramic X-ray apparatus is used, data that is obtained by scanning the plaster cast of the oral cavity of the patient may be additionally necessary to convert the current state of teeth of the patient into 3D data.

In addition, the scanners that scan the current state of teeth of the patient include a 3D scanner for oral cavity.

Specifically, FIG. 12 illustrates an upper tooth 502 and a lower tooth 503 of the patient. Then, the upper tooth 502 and the lower tooth 503 of the patient are scanned with a mouthpiece inserted between the upper tooth 502 and the lower tooth 503 using the scanner, in order to separately obtain data on a state of the upper tooth 502 and data on a state of the lower tooth 503.

Figure 13:
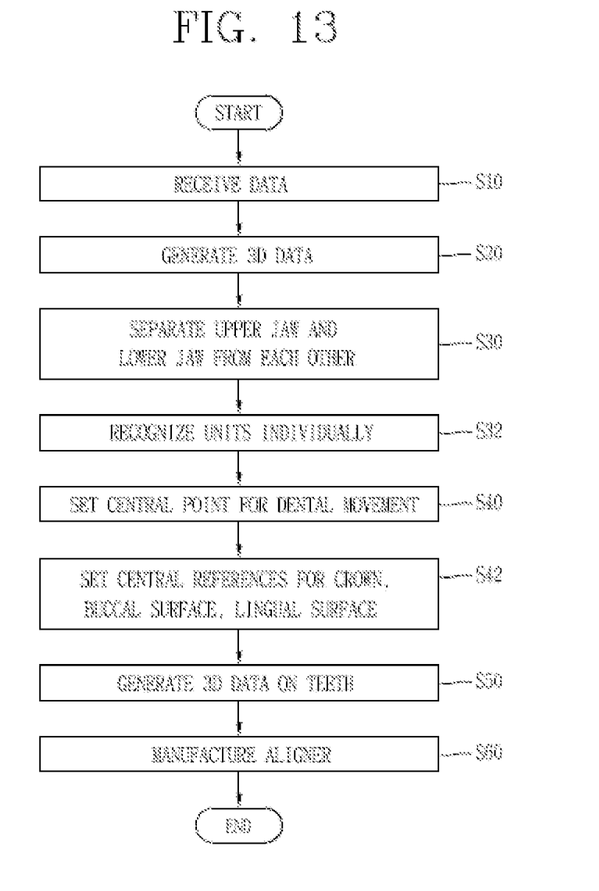
FIG. 13 is a flowchart illustrating a method of manufacturing a clear aligner according to an embodiment of the present invention.

FIG. 13 is a flowchart illustrating a method of manufacturing a clear aligner according to an embodiment of the present invention.

The method of manufacturing the clear aligner using an apparatus for generating dental data for manufacturing an aligner according to one embodiment of the present invention includes Step S10 of receiving data on a current state of teeth of a patient from a scanner that scans the current state of teeth of the patient, Step S20 of generating 3D data on a state of an oral cavity, based on the data, Step S30 of separating an upper jaw and a lower jaw from each other in the 3D data, Step S40 of setting a central point for dental movement to be on a root of a tooth with the upper jaw and the lower jaw being separated from each other, a Step S50 of generating 3D data on the tooth that is moved a predetermined distance from the central point for dental movement, and Step S60 of manufacturing the clear aligner based on the 3D data on the moved tooth.

The 3D data on the tooth may be data on a dental periodontal complex that includes the tooth, an alveolar bone, and a gingiva, as described above.

The method of manufacturing the clear aligner may further include Step S32 of separating teeth from each other and individually recognizing the teeth as units of dental movement after Step S30 of separating the upper jaw and the lower jaw.

In addition, in Step S50 of generating the 3D data on the tooth, the dental periodontal complex is moved in such a manner that dental alignment is performed with high precision.

In Step S50 of generating the 3D data on the tooth, the predetermined distance is determined in such a manner that a movement-target tooth is moved a distance of between 1.0 mm and 1.5 mm per month. Then, 3D data on a distance (for example, a distance of between 1.0 mm to 1.5 mm per month) that the movement-target has moved for a predetermined period of time is generated.

For example, in a case where the number of movement-target teeth is 3 and a distance that the teeth that can be moved the greatest distance per month is moved is 3 mm, when the greatest distance per month is 1 mm, a period of three months is necessary to accomplish the dental alignment. At this time, in Step S50 of generating the 3D data on the tooth, three pieces of 3D data on the three teeth, of which one is moved the greatest distance of 1 mm per month, are moved, respectively, are generated from the original data.

In addition, in order to predict a state of the face of the patient that will result after the dental alignment is performed, in addition to the pieces of data on the three teeth, data on the state of the face of the patient, which results when one of the three teeth is moved the greatest distance of 1 mm per month, may be generated.

Furthermore, in Step S50 of generating the 3D data on the tooth, after each dental periodontal complex is moved for a predetermined period of time, the central point for dental movement is newly set based on the moved dental periodontal complex.

In a case where a distance that the tooth that can be moved the greatest distance per month is moved is 3 mm and in a case where the pieces of data on the teeth, one of which is moved a distance of 1 mm per month, are generated, after the teeth is first moved a distance of 1 mm, the central point for movement of the dental periodontal complex is newly set for the second time, based on the moved dental periodontal complex. Thereafter, the teeth are moved a distance of 1 mm, based on the central point for dental movement, which is newly set in the data, and then the central point for dental movement is set newly, based on the moved dental periodontal complex.

The reason for newly setting the central point for dental movement is because, while the dental alignment is in process, the dental periodontal complex is moved. While the teeth are moved, a portion of each of dental roots is out of the gum and thus the length of each of the dental roots is changed. For this reason, the central point for dental movement is changed while the dental alignment is in progress. Therefore, the central point for movement of the tooth is newly set after the tooth has been moved for a predetermined period of time.

In the data on the dental periodontal complex, the teeth, the alveolar bone, and the gingiva of the patient are distinguishably expressed in different colors.

In addition, the method of manufacturing the clear aligner may further include a step of setting a central reference point to be on the crown, the buccal surface, and the lingual surface of each tooth after Step S40 of setting the central point for dental movement.

Then, in Step S60 of manufacturing the clear aligner, the clear aligner may be manufactured using any one of a method of sintering PET powder using a laser, a method of layering PET filaments using heat or adhesive, or a method of forming the PET filaments into a shape of the clear aligner above a melting point using a 3D printer and then solidifying the clear aligner.

In addition, the clear aligner may be manufactured by forming liquid-state PET into a specific shape based on the data, using a laser.

Then, when manufacturing the clear aligner, the method of layering PET filaments, the method of sintering PET powder using a laser, or the method of solidifying a PET solution using a laser may be used.

In addition, the method of manufacturing the clear aligner may further include Step S32 of recognizing the teeth as units of dental movement after Step S30 of separating the upper jaw and the lower jaw from each other.

Furthermore, the method of manufacturing the clear aligner may further include Step S42 of setting the central reference point to be on each of the crown, the buccal surface, and the lingual surface, after Step S40 of setting the central point for dental movement.

The effects of the apparatus for generating dental data for manufacturing an aligner and the method of manufacturing the clear aligner using the apparatus according to the present invention are as follows.

According to at least one of the embodiments of the present invention, the 3D data on the teeth of the patient is generated based on the data that is obtained by the fan beam CT apparatus, the cone beam apparatus, the panoramic X-ray apparatus, or the 3D scanner, and the data on the plaster case of the oral cavity, and thus various types of scanners can be used.

In addition, according to at least one of the embodiments of the present invention, when setting the central point for dental movement, the central point for dental movement is set considering the dental root, the gingiva, and the alveolar bone, as well as the tooth, and thus the dental alignment is performed with more precision.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A non-transitory computer readable medium having computer executable instructions thereon, wherein the instructions perform a method of aligning a target tooth in multiple stages based on a current arrangement of teeth of a patient, the method comprising:
   receiving data on a current state of the teeth of the patient from a scanner that scans the current state of the teeth of the patient,
   generating a state of the teeth of the patient and the vicinity of the teeth as 3D data, based on the data received from the scanner,
   setting a central point for dental movement in the 3D data,
   setting each central reference for a crown, a buccal surface, and a lingual surface of the tooth in the 3D data, and
   setting a reference for a dental root point in the 3D data, and wherein
   setting the central point for dental movement comprises recognizing a tooth, an alveolar bone that encloses the tooth, and a gingiva that encloses the alveolar bone, and wherein
   the central point for dental movement is set with respect to a single-rooted tooth with one root to be positioned at a distance of 40% to 42% of the root of the tooth enclosed by an alveolar bone downward from the top of the alveolar bone, and the central point for dental movement of which is set with respect to a multi-rooted tooth to be positioned at a distance of between 1 and 2 mm downward from the furcation from which the root of the tooth bifurcates.

2. The medium of claim 1, wherein the scanner is a fan beam computed tomography (fan beam CT) apparatus,
   wherein data that is received from the fan beam apparatus includes
   first data for expressing a state where the teeth are engaged with each other in order to check shapes of the teeth that are engaged with each other, and
   second data for expressing a state where a wax is attached to a gingiva or a mouthpiece is inserted into an oral cavity of the patient in such a manner that a space is secured between the gingiva and adjacent lips, in order to check a thickness of the gingiva.

3. The medium of claim 2, wherein the generating step further comprises recognizing the thickness of the gingiva based on the first data and the second data, and generating the 3D data for expressing the teeth and an alveolar bone that encloses the teeth, along with the gingiva that encloses the alveolar bone.

4. The medium of claim 3, wherein the method further comprises expressing the teeth, the alveolar bone, and the gingiva in different colors.

5. The medium of claim 3, wherein the generating step further comprises separating an upper jaw and a lower jaw from each other in the 3D data.

6. The medium of claim 3, wherein the generating step further comprises separating the teeth of the patient from each other as units of dental movement based on the 3D data, and recognizing the teeth individually in such a manner that each of the teeth is able to be moved.

7. The medium of claim 1, wherein the method further comprises moving the tooth by a predetermined distance from the central point for dental movement.

8. The medium of claim 7, wherein the step of setting a central point further comprises moving the tooth by the predetermined distance, and setting the central point for dental movement based on data on the moved tooth.

9. The medium of claim 7, wherein the step of moving the tooth further comprises moving a dental periodontal complex that includes the tooth, the alveolar bone that encloses the tooth, and the gingiva that encloses the alveolar bone.

10. The medium of claim 9, wherein the method further comprises combining data on a photograph of the patient with the current state of the teeth of the patient to express in detail a state of the teeth that will result after dental alignment is performed.

11. The medium of claim 1, wherein the scanner is at least one among a cone beam computed tomography (cone beam CT) apparatus, a panoramic X-ray (panoramic radiograph) apparatus, and a 3D scanner.

12. The medium of claim 11, wherein the generating step, data that is used as basic data includes the data that is received from the scanner, and data that is obtained, as a supplement to the data that is received from the scanner, by modelling a plaster cast of an oral cavity of the patent.

13. A method of manufacturing a clear aligner using an apparatus for generating dental data for manufacturing an aligner, the method comprising:
   receiving data on a current state of teeth of a patient from a scanner that scans the current state of teeth of the patient;
   generating 3D data on a state of an oral cavity, based on the data;
   separating an upper jaw and a lower jaw from each other in the 3D data;
   separating teeth from each other and individually recognizing the teeth as units of dental movement;
   setting a central point for dental movement to be on a root of a tooth in a state where the upper jaw and the lower jaw is separated from each other;
   generating 3D data on the tooth that is moved a predetermined distance from the central point for dental movement; and
   manufacturing the clear aligner based on the 3D data on the moved tooth, wherein
   the 3D data on the tooth is data on a dental periodontal complex that includes the tooth, an alveolar bone, and a gingiva, and wherein
   in the generating of the 3D data on the tooth, the dental periodontal complex is moved in such a manner that dental alignment is performed with high precision.

14. The method of claim 13, wherein in the generating of the 3D data on the tooth, a distance that an alignment target tooth is moved for one month is set to 1.0 to 1.5 mm, multiple pieces of 3D data on the alignment target tooth are generated every predetermined period of time, and a moved state of the alignment target tooth and the contour of the face of the patient are generated.

15. The method of claim 14, wherein in the generating of the 3D data on the tooth, after each dental periodontal complex is moved for a predetermined period of time, the central point for dental movement is newly set based on the moved dental periodontal complex.

16. The method of claim 13, wherein in the clear aligner is manufactured using any one of a method of sintering PET powder using a laser, a method of layering PET filaments using heat or adhesive, or a method of forming the PET filaments into a shape of the clear aligner above a melting point using a 3D printer and then solidifying the clear aligner.

* * * * *